US008900157B2

(12) United States Patent
Yamashita et al.

(10) Patent No.: US 8,900,157 B2
(45) Date of Patent: Dec. 2, 2014

(54) ELECTRONIC SPHYGMOMANOMETER AND BLOOD PRESSURE MEASUREMENT CONTROL METHOD

(75) Inventors: Shingo Yamashita, Kyoto (JP); Yoko Shimose, Hirakata (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 247 days.

(21) Appl. No.: 13/060,417

(22) PCT Filed: Aug. 14, 2009

(86) PCT No.: PCT/JP2009/064339
§ 371 (c)(1),
(2), (4) Date: Feb. 23, 2011

(87) PCT Pub. No.: WO2010/026862
PCT Pub. Date: Mar. 11, 2010

(65) Prior Publication Data
US 2011/0160598 A1    Jun. 30, 2011

(30) Foreign Application Priority Data
Sep. 2, 2008 (JP) ................................. 2008-225086

(51) Int. Cl.
*A61B 5/02* (2006.01)
*A61B 5/0225* (2006.01)
*A61B 5/021* (2006.01)
*A61B 5/022* (2006.01)

(52) U.S. Cl.
CPC ........... *A61B 5/0225* (2013.01); *A61B 5/02141* (2013.01); *A61B 5/02225* (2013.01)
USPC ....................................................... 600/493

(58) Field of Classification Search
CPC .. A61B 5/021; A61B 5/0215; A61B 5/02152; A61B 5/02216; A61B 5/022; A61B 5/02208; A61B 5/02225; A61B 5/023; A61B 5/0235; A61B 5/02233
USPC .................................................. 600/485–499
See application file for complete search history.

(56) References Cited

U.S. PATENT DOCUMENTS

| 5,438,983 A * | 8/1995 | Falcone ........................ 600/301 |
| 2007/0038132 A1 | 2/2007 | Kishimoto et al. |
| 2008/0082007 A1 * | 4/2008 | Friedman ...................... 600/494 |

FOREIGN PATENT DOCUMENTS

| GB | 2281780 A | 3/1995 |
| JP | 2001-309895 A | 11/2001 |

(Continued)

OTHER PUBLICATIONS

M. Golara, et al., "Inflationary oscillometry provides accurate measurement of blood pressure in pre-eclampsia," BJOG; an International Journal of Obstetrics and Gynaecology, Oct. 2002, vol. 109, pp. 1143-1147; 5 pages.

(Continued)

*Primary Examiner* — Patricia Mallari
*Assistant Examiner* — Vasuda Ramachandran
(74) *Attorney, Agent, or Firm* — Osha Liang LLP

(57) ABSTRACT

A blood pressure measurement control method for controlling the measurement of a blood pressure according to an oscillometric method has the steps of determining whether to employ a depressurization measurement method or a pressurization measurement method to measure the blood pressure according to a person to be measured, performing a measurement process of the blood pressure in a depressurization process when determined to measure the blood pressure with the depressurization measurement method, performing a measurement process of the blood pressure in a pressurization process when determined to measure the blood pressure with the pressurization measurement method, and outputting the measured blood pressure value.

5 Claims, 16 Drawing Sheets

(56) References Cited

FOREIGN PATENT DOCUMENTS

| JP | 2005-185681 A | 7/2005 |
|----|---------------|--------|
| JP | 2007-130319 A | 5/2007 |

OTHER PUBLICATIONS

Patent Abstracts of Japan, Publication No. 2007-130319, dated May 31, 2007, 1 page.
Patent Abstracts of Japan, Publication No. 2001-309895, mailed on Nov. 6, 2001, 1 page.
Patent Abstracts of Japan, Publication No. 2005-185681, dated Jul. 14, 2005, 1 page.
International Search Report issued in PCT/JP2009/064339, mailed on Sep. 8, 2009, w/translation, 5 pages.
Office Action in corresponding Russian application No. 2011107937 dated Jul. 8, 2013 (12 pages).
Moneli Golara, et al.; "Inflationary oscillometry provides accurate measurement of blood pressure in pre-eclampsia"; BJOG: an Internatioanl Journal of Obstetrics and Gynaecology; vol. 109, pp. 1143-1147; Oct. 2002 (5 pages).
Office Action Issued in Chinese Application No. 200980134344.9, Dated Jun. 7, 2013 (14 Pages with English Translation).
Golara, Moneli, et al. "Inflationary oscillometry provides accurate measurement of blood pressure in pre-eclampsia", BJOG: an International Journal of Obstetrics and Gynaecology, Oct. 2002, vol. 109, pp. 1143-1147 (5 pages).

* cited by examiner

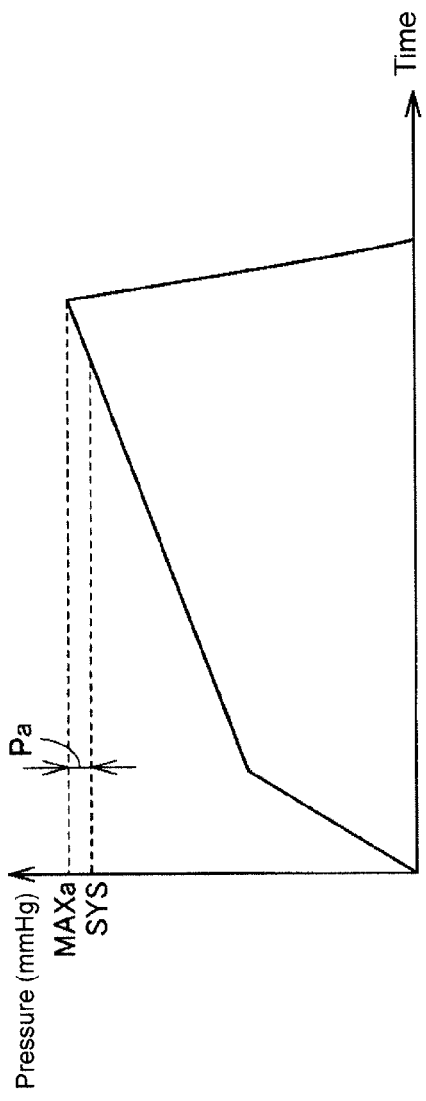
Fig. 9A  (a) Pressurization measurement method
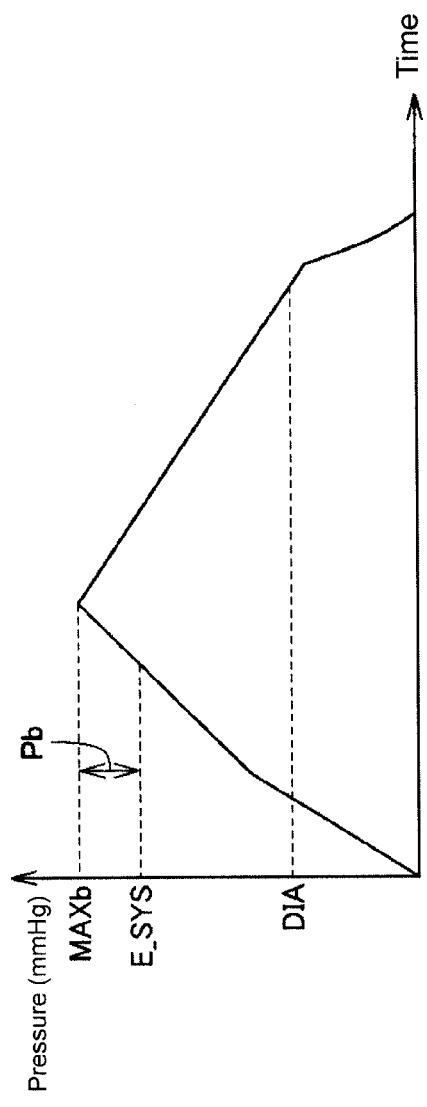
Fig. 9B  (b) Depressurization measurement method

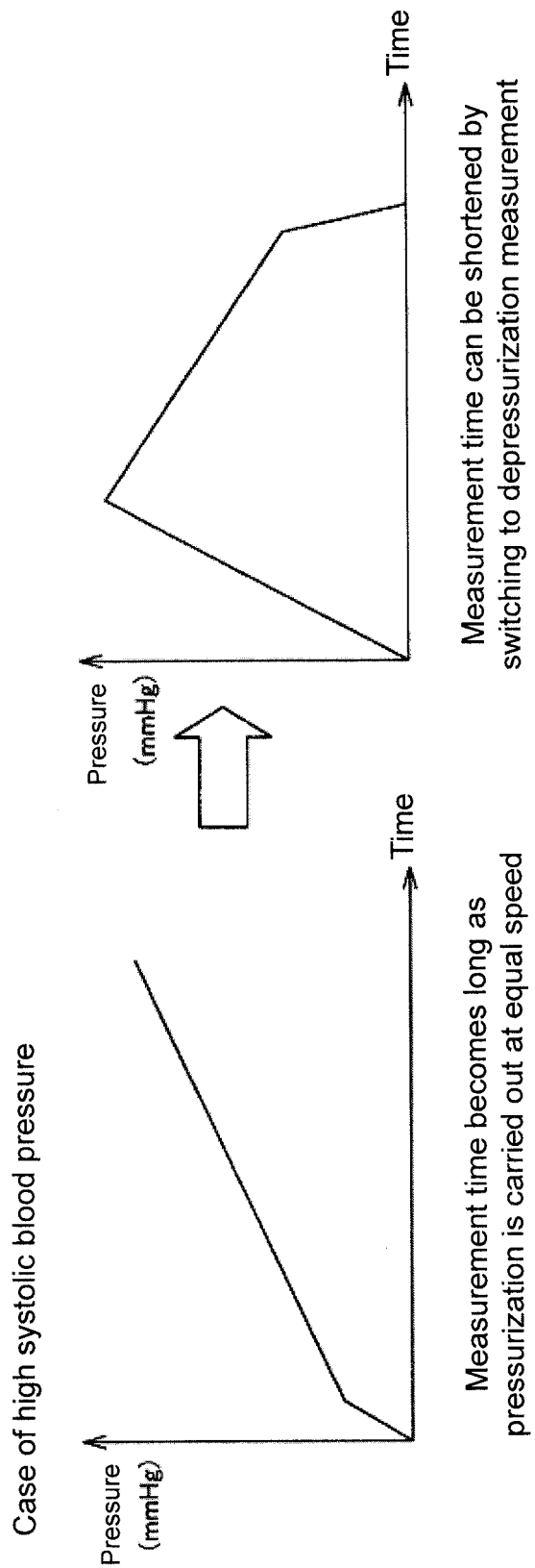

Fig. 14A (a) Arm of standard thickness

Fig. 14B (b) Thick arm

ELECTRONIC SPHYGMOMANOMETER AND BLOOD PRESSURE MEASUREMENT CONTROL METHOD

BACKGROUND OF THE INVENTION

1. Technical Field

The present invention relates to electronic sphygmomanometers and blood pressure measurement control methods, and in particular, to an electronic sphygmomanometer and a blood pressure measurement control method for measuring the blood pressure according to the oscillometric method.

2. Background Art

In recent years, it is recognized that not only the measurement in medical institutions but daily management at homes is important for the measurement of the blood pressure. Use is made for the diagnosis of cardiovascular complications, which probability of occurrence in early morning is high, such as early morning high blood pressure, and the like by grasping the blood pressure fluctuation by time zone.

The sphygmomanometer for measuring the blood pressure according to the oscillometric method includes a type that measures the blood pressure during pressurization (hereinafter referred to as "pressurization measurement method") and a type that measures the blood pressure during depressurization (hereinafter referred to as "depressurization measurement method"). It is generally assumed that the same measurement value can be obtained regardless of which method was used for the measurement, and only one of the measurement methods is loaded on the sphygmomanometer.

Japanese Unexamined Patent Publication No. 2001-309895 (patent document 1), on the other hand, describes switching the two measurement methods for measurement. Specifically, the vein relative pressure is measured on the peripheral side than the arm band at the time of measuring the blood pressure in artery hemostasis by the arm band, and remeasurement is urged if the difference of the artery pressure value and the vein relative pressure is lower than or equal to a predetermined value to prevent wrong measurement of the blood pressure by blood stasis. It is stated that the measurement method is switched from the depressurization measurement method to the pressurization measurement method in remeasurement.

Patent Document 1: Japanese Unexamined Patent Publication No. 2001-309895

SUMMARY

As described above, since similar measurement result is usually obtained regardless of whether the pressurization measurement method or the depressurization measurement method is used for the measurement, and hence, only one of the measurement methods is mounted in the conventional sphygmomanometer. Proposal has been made that even if both measurement methods are mounted, switch is made to the pressurization method only if the measurement value has no reliability when measured with the depressurization measurement method as in Japanese Unexamined Patent Publication No. 2001-309895 (patent document 1).

Therefore, the measurement method cannot be flexibly switched according to the person to be measured.

One or more embodiments of the present invention provides an electronic sphygmomanometer and a blood pressure measurement control method capable of measuring the blood pressure with a measurement method suited for every person to be measured.

In accordance with an aspect of the present invention, there is provided an electronic sphygmomanometer for measuring a blood pressure according to an oscillometric method, the electronic sphygmomanometer including: a cuff to be wrapped around a predetermined measurement site; an adjustment unit for adjusting a pressure in the cuff by pressurization and depressurization; a pressure detection unit for detecting a cuff pressure representing the pressure in the cuff; and a control unit for performing a control for measuring the blood pressure; wherein the control unit includes, a determination unit for determining with which measurement method, a depressurization measurement method or a pressurization measurement method, to measure the blood pressure according to a person to be measured, a first measurement processing unit for performing a measurement process of the blood pressure in a depressurization process when determined by the determination unit to measure the blood pressure with the depressurization measurement method, and a second measurement processing unit for performing a measurement process of the blood pressure in a pressurization process when determined by the determination unit to measure the blood pressure with the pressurization measurement method.

According to one or more embodiments of the present invention, the electronic sphygmomanometer further includes: an input accepting unit accepting input information from a user; wherein the determination unit determines the measurement method based on the input information.

According to one or more embodiments of the present invention, the input accepting unit accepts information on whether or not the person to be measured is a pregnant woman as the input information; and the determination unit determines the pressurization measurement method if the person to be measured is a pregnant woman.

According to one or more embodiments of the present invention, the input accepting unit accepts information on whether or not an arm of the person to be measured is thick as the input information; and the determination unit determines the pressurization measurement method if the arm of the person to be measured is thick.

According to one or more embodiments of the present invention, the electronic sphygmomanometer further includes: a storage unit for storing past blood pressure values measured by the first measurement processing unit and the second measurement processing unit; wherein the determination unit determines the measurement method assumed to have shorter measurement time of the depressurization measurement method and the pressurization measurement method for the measurement method of the person to be measured based on the past blood pressure values stored in the storage unit.

According to one or more embodiments of the present invention, the electronic sphygmomanometer further includes: a storage unit for storing past blood pressure values measured by the first measurement processing unit and the second measurement processing unit; wherein the determination unit determines the measurement method assumed to have less pain by compression of the depressurization measurement method and the pressurization measurement method for the measurement method of the person to be measured based on the past blood pressure values stored in the storage unit.

According to one or more embodiments of the present invention, the determination unit determines the pressurization measurement method when the systolic blood pressure of the person to be measured is higher than or equal to a predetermined value.

According to one or more embodiments of the present invention, the measurement method set in advance by the person to be measured is determined as the measurement method of the person to be measured if an automatic switching function of the measurement method is set to invalid by the person to be measured.

According to one or more embodiments of the present invention, the electronic sphygmomanometer further includes: a display unit for displaying the measurement result of the blood pressure, wherein the display unit further displays information for specifying the method used for the measurement of the depressurization measurement method and the pressurization measurement method.

According to one or more embodiments of the present invention, the determination unit determines the measurement method corresponding to the person to be measured by comparing the measurement results of the first measurement processing unit and the second measurement processing unit.

According to one or more embodiments of the present invention, the first measurement processing unit transitions to a depressurization control at slow speed when the systolic blood pressure is estimated in the pressurization process at a speed faster than the depressurization process.

According to one or more embodiments of the present invention, the second measurement processing unit rapidly depressurizes when the systolic blood pressure is detected in the pressurization process at slow speed.

In accordance with another aspect of the present invention, there is provided a blood pressure measurement control method for controlling the measurement of a blood pressure according to an oscillometric method, the method including the steps of: determining with which measurement method, a depressurization measurement method or a pressurization measurement method, to measure the blood pressure according to a person to be measured; performing a measurement process of the blood pressure in a depressurization process when determined to measure the blood pressure with the depressurization measurement method; performing a measurement process of the blood pressure in a pressurization process when determined to measure the blood pressure with the pressurization measurement method; and outputting the measured blood pressure value.

In the electronic sphygmomanometer, the determination unit desirably determines the depressurization measurement method when the systolic blood pressure of the person to be measured is higher than or equal to a predetermined value to determine the measurement method assumed to have shorter measurement time for the measurement method of the person to be measured. Alternatively, the determination unit desirably determines the pressurization measurement method when the pulse pressure of the person to be measured is higher than or equal to a predetermined value.

According to one or more embodiments of the present invention, the blood pressure can be measured with the measurement method suited for every person to be measured of the depressurization measurement method and the pressurization measurement method.

BRIEF DESCRIPTION OF THE DRAWINGS

FIGS. 9A and 9B are views showing the difference in the maximum pressure value by the pressurization measurement method and the depressurization measurement method.

FIGS. 10A and 10B are views showing the difference in measurement time by the pressurization measurement method and the depressurization measurement method for when the systolic blood pressure is high.

DETAILED DESCRIPTION

Figure 1:
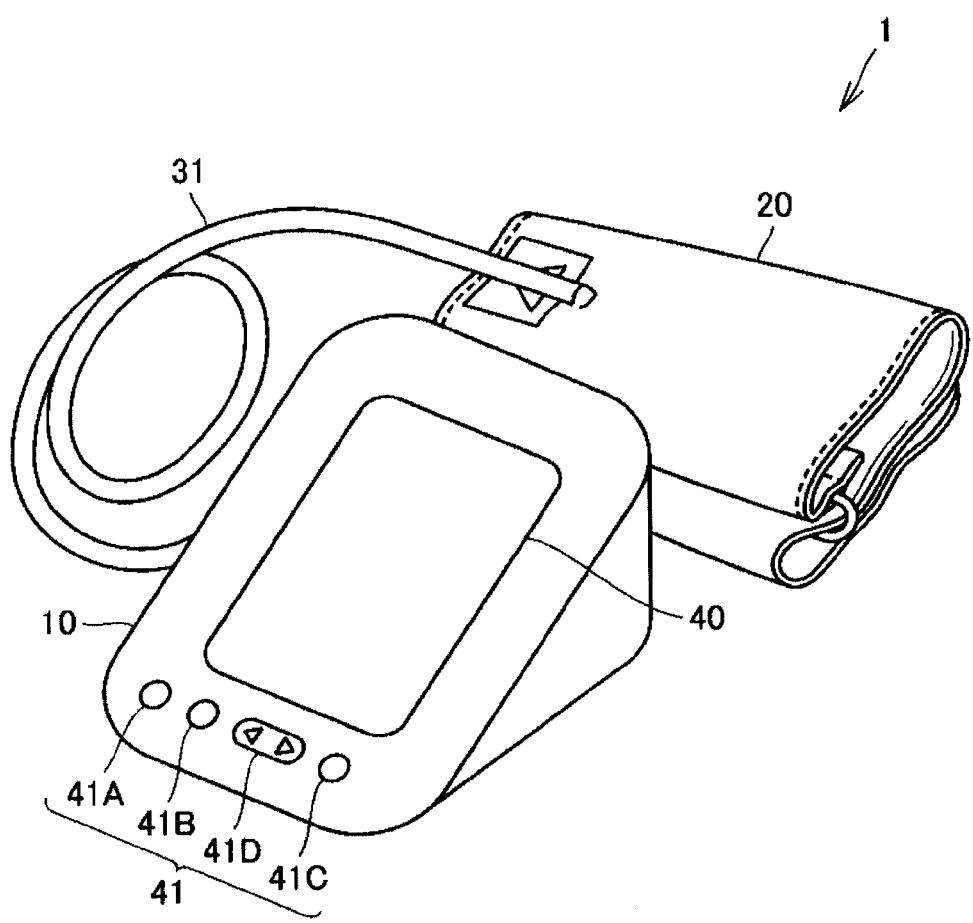
FIG. 1 is a perspective view of an outer appearance of a sphygmomanometer according to a first embodiment of the present invention.

Embodiments of the present invention will be described in detail with reference to the drawings. The same reference numerals are denoted for the same or corresponding portions in the figures, and the description thereof will not be repeated. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

[First Embodiment]
<Outer Appearance and Configuration>

The outer appearance and the configuration of an electronic sphygmomanometer (hereinafter abbreviated as "sphygmomanometer") according to a first embodiment of the present invention will be described first.

(Regarding Outer Appearance)

FIG. 1 is a perspective view of an outer appearance of a sphygmomanometer 1 according to a first embodiment of the present invention. The sphygmomanometer 1 measures the blood pressure according to the oscillometric method.

With reference to FIG. 1, the sphygmomanometer 1 includes a main body 10, a cuff 20 that can be wrapped around a predetermined measurement site (e.g., upper arm) of the person to be measured, and an air tube 31 for connecting the main body 10 and the cuff 20. A display unit 40 configured by liquid crystals and the like, and an operation unit 41 for accepting instructions from a user (representatively, person to be measured) are arranged on the surface of the main body 10.

The operation unit 41 includes a power switch 41A for accepting an input of the instruction to turn ON or OFF the power supply, a measurement switch 41B for accepting the instruction to start the measurement, a set switch 41C for accepting the instruction for various types of setting processes and reading of storage values, and a cursor switch 41D.

(Regarding Hardware Configuration)

Figure 2:
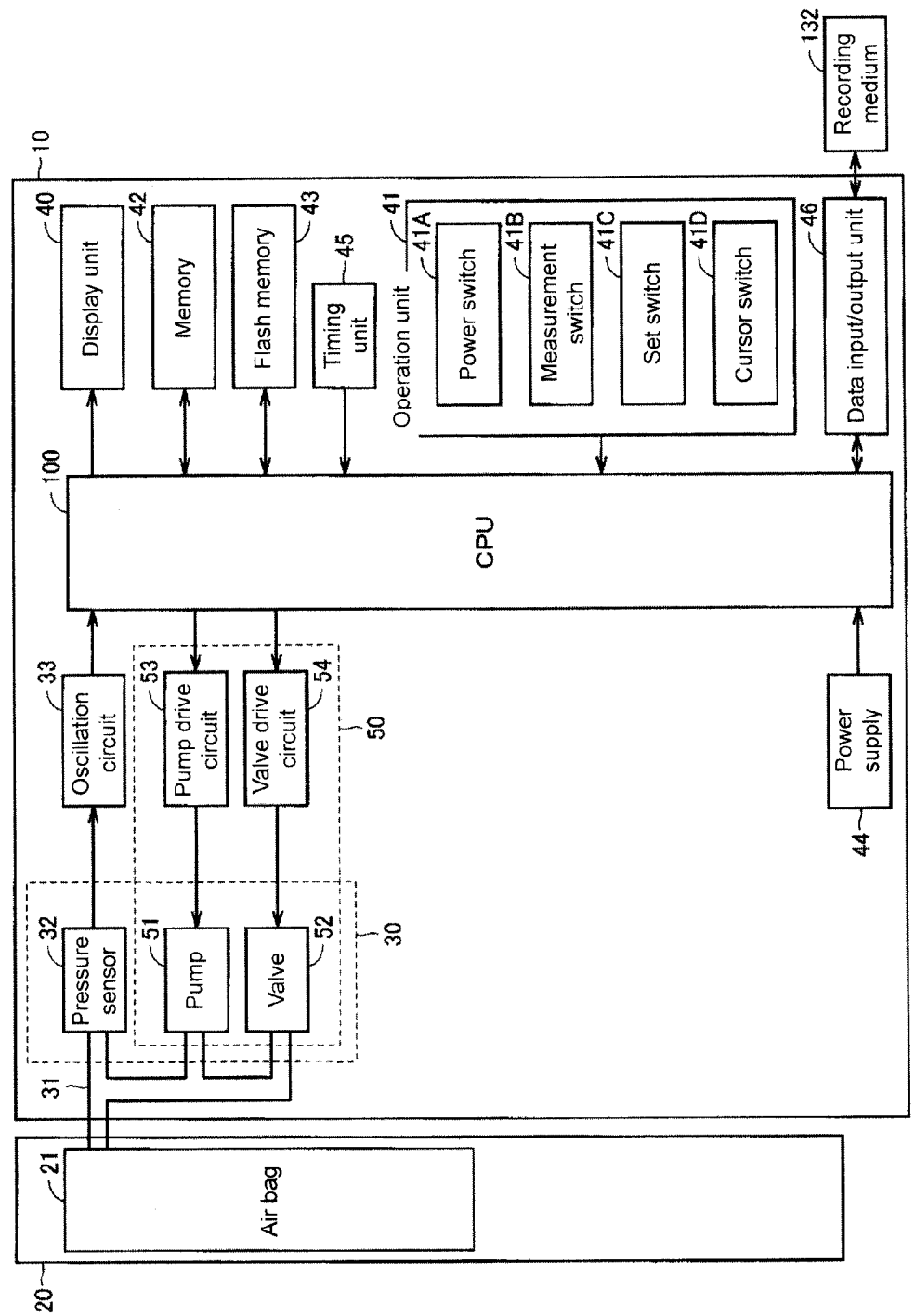
FIG. 2 is a block diagram showing the hardware configuration of the electronic sphygmomanometer according to the first embodiment of the present invention.

FIG. 2 is a block diagram showing the hardware configuration of the sphygmomanometer 1 according to the first embodiment of the present invention.

With reference to FIG. 2, the cuff 20 of the sphygmomanometer 1 includes an air bag 21. The air bag 21 is connected to an air system 30 by means of the air tube 31.

In addition to the display unit 40 and the operation unit 41, the main body 10 includes a CPU (Central Processing Unit) 100 for controlling each unit in a concentrated manner and for carrying out various calculation processes, a memory 42 for storing programs for causing the CPU 100 to perform a predetermined operation and various data, a non-volatile memory (e.g., flash memory) 43 for storing the measured blood pressure, a power supply 44 for supplying power to the CPU 100, a timing unit 45 for performing the timing operation, and a data input/output unit 46 for receiving the input of data from the outside.

The air system 30 includes a pressure sensor 32 for detecting the pressure (cuff pressure) in the air bag 21, a pump 51 for supplying air to the air bag 21 to pressurize the cuff pressure, and a valve 52 that opens and closes to exhaust or enclose the air of the air bag 21.

The main body 10 also includes an oscillation circuit 33, a pump drive circuit 53, and a valve drive circuit 54 in association with the air system 30.

The pressure sensor 32 is a capacitance type pressure sensor, where the capacitance value changes according to the cuff pressure. The oscillation circuit 33 outputs a signal of an oscillating frequency corresponding to the capacitance value of the pressure sensor 32 to the CPU 100. The CPU 100 converts the signal obtained from the oscillation circuit 33 to pressure, and detects the pressure. The pump drive circuit 53 controls the drive of the pump 51 based on a control signal provided from the CPU 100. The valve drive circuit 54 performs the open/close control of the valve 52 based on a control signal provided from the CPU 100.

The pump 51, the valve 52, the pump drive circuit 53, and the valve drive circuit 54 configure an adjustment unit 50 for adjusting the cuff pressure. It should be recognized that the device for adjusting the cuff pressure is not limited thereto.

The data input/output unit 46 performs read and write of programs and data with respect to a removable recording medium 132. Alternatively, the data input/output unit 46 may transmit and receive programs and data through a communication line with respect to an external computer (not shown).

Although the cuff 20 includes the air bag 21, the fluid supplied to the cuff 20 is not limited to air and may be liquid or gel. Alternatively, the fluid is not the sole case, and uniform fine particles such as micro-beads may be used.

(Regarding Outline of Functions and Function Configuration)

The outline of the functions of the sphygmomanometer 1 will be described prior to describing the specific function configuration of the sphygmomanometer 1 according to the present embodiment.

The conventional electronic sphygmomanometer for the arm typically uses the depressurization measurement method due to historical background and the like. The electronic sphygmomanometer for the wrist, on the other hand, typically uses the pressurization measurement method due to limitation in the flow rate of the pump (component is desirably made small). It is normally said that the results do not differ regardless of which measurement method is used for the measurement, and hence only either one of the measurement methods is mounted.

However, a research result that the pressurization measurement method can more accurately measure the blood pressure in pregnant women has been recently publicized. ("Inflationary oscillometry provides accurate measurement of blood pressure in pre-eclampsia" Moneli Golara, Amanda Benedict, Clare Jones, Manjit Randhawa, Lucilla Poston, Andrew H. Shennan, BJOG; an international Journal of Obstetrics and Gynaecology, October 2002, Vol. 109, pp. 1143-1147)

Therefore, the pressurization method according to one or more embodiments of the present invention is for the pregnant women when attempting to accurately measure the blood pressure. However, some users prefer the depressurization measurement method as the depressurization measurement method is the standard.

The sphygmomanometer 1 according to the present embodiment mounts both the depressurization measurement algorithm and the pressurization measurement algorithm. The blood pressure can be measured with the measurement method suited to the person to be measured based on the input information of the user (representatively, person to be measured). In the following description, assumption is that the user (person to be measured) of the sphygmomanometer 1 exists in plurals for the sake of convenience, but the user of the sphygmomanometer 1 may be one.

Figure 3:
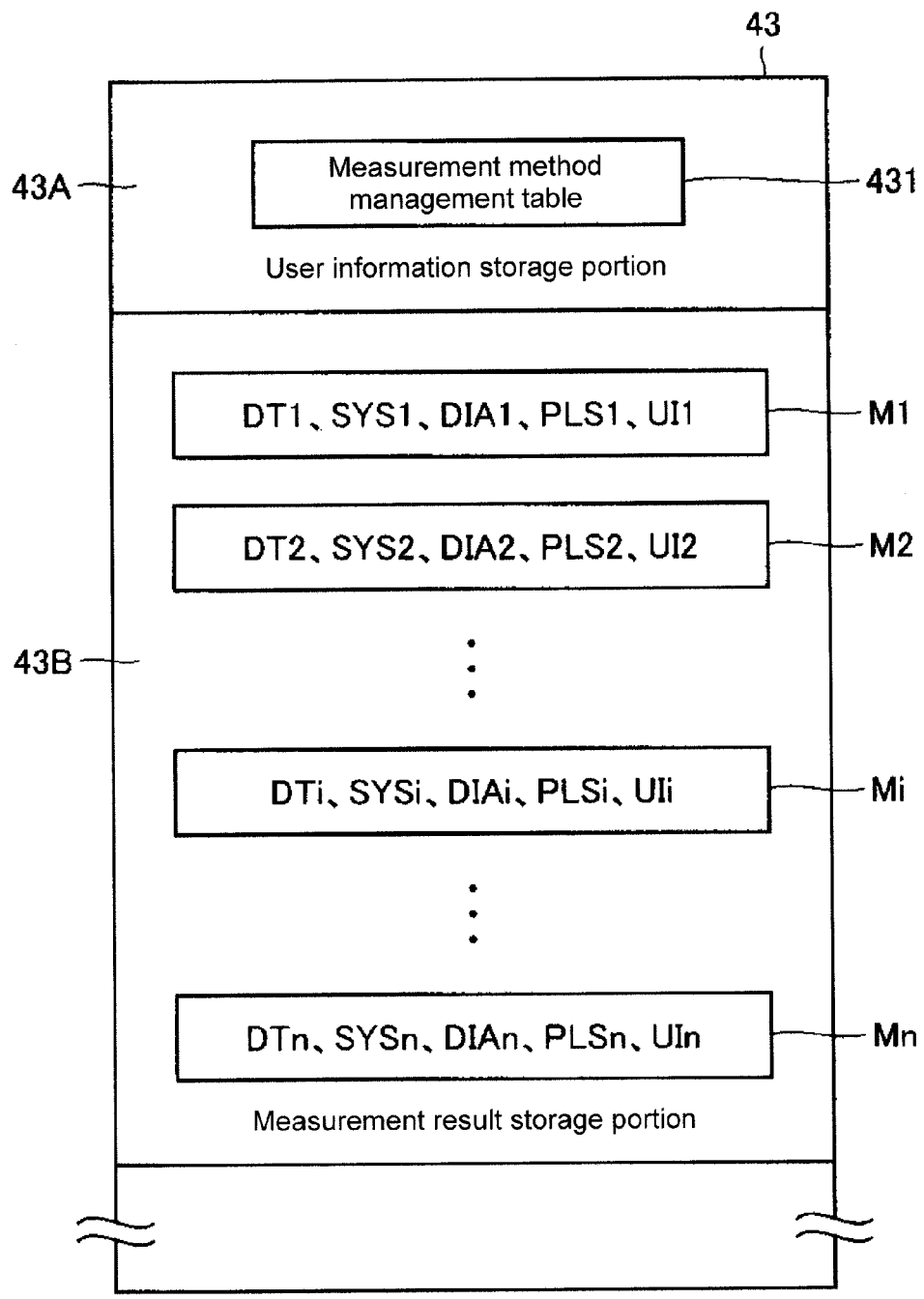
FIG. 3 is a view showing one example of a data structure of a flash memory in the first embodiment of the present invention.

FIG. 3 is a view showing one example of a data structure of the flash memory 43 in the first embodiment of the present invention.

With reference to FIG. 3, the flash memory 43 includes a user information storage portion 43A, and a measurement result storage portion 43B. The user information storage portion 43A stores a measurement method management table 431.

Figure 4:
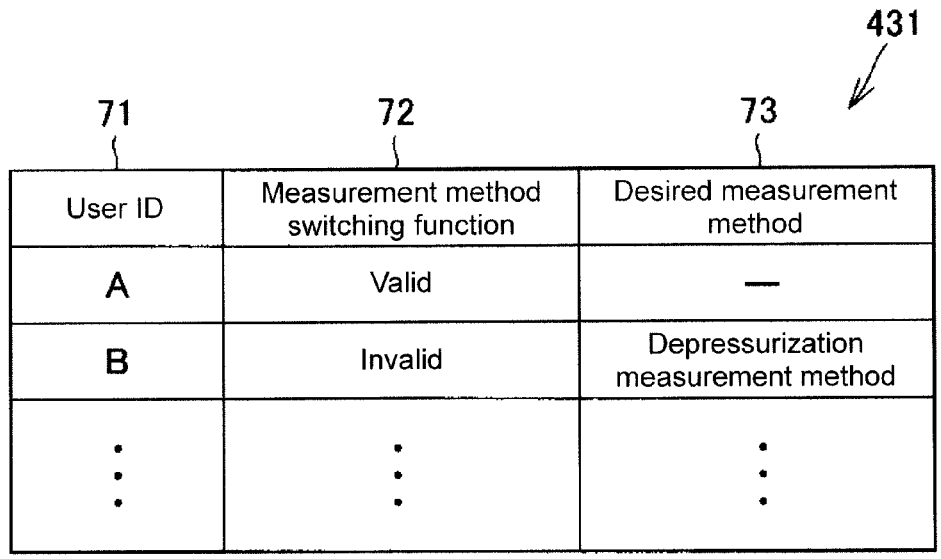
FIG. 4 is a view showing one example of a data structure of the measurement method management table in the flash memory of the first embodiment of the present invention.

FIG. 4 is a view showing one example of a data structure of the measurement method management table 431.

With reference to FIG. 4, the measurement method management table 431 is configured by three items, that is, a "user ID" item 71, a "measurement method switching function" item 72, and a "desired measurement method" item 73. The identification information of the person to be measured is stored in the user ID item 71. "Valid" or "invalid" is stored in the measurement method switching function item 72. The method of either the "pressurization measurement method" or the "depressurization measurement method" is stored in the desired measurement method item 73. The information of either one of the measurement method may be stored in the item 73 only when the measurement method switching function item 72 is invalid.

The setting information for every person to be measured is input by the user in advance.

Referring again to FIG. 3, the measurement result storage portion 43B stores a plurality of measurement result data Mi (i=1, 2, . . . , n). The measurement result data Mi includes date and time data DTi representing the measurement date and time, systolic blood pressure data SYSi representing the systolic blood pressure, diastolic blood pressure data DIAi representing the diastolic blood pressure, pulse rate data PLSi representing the pulse rate, and user ID data Uli representing the user identification information. Therefore, the measurement value (systolic blood pressure, diastolic blood pressure, pulse wave number) and the user identification information are stored in correspondence to each other for every measurement. The storage form is not limited thereto as long as the measurement value and the user identification information are corresponded to each other.

Figure 5:
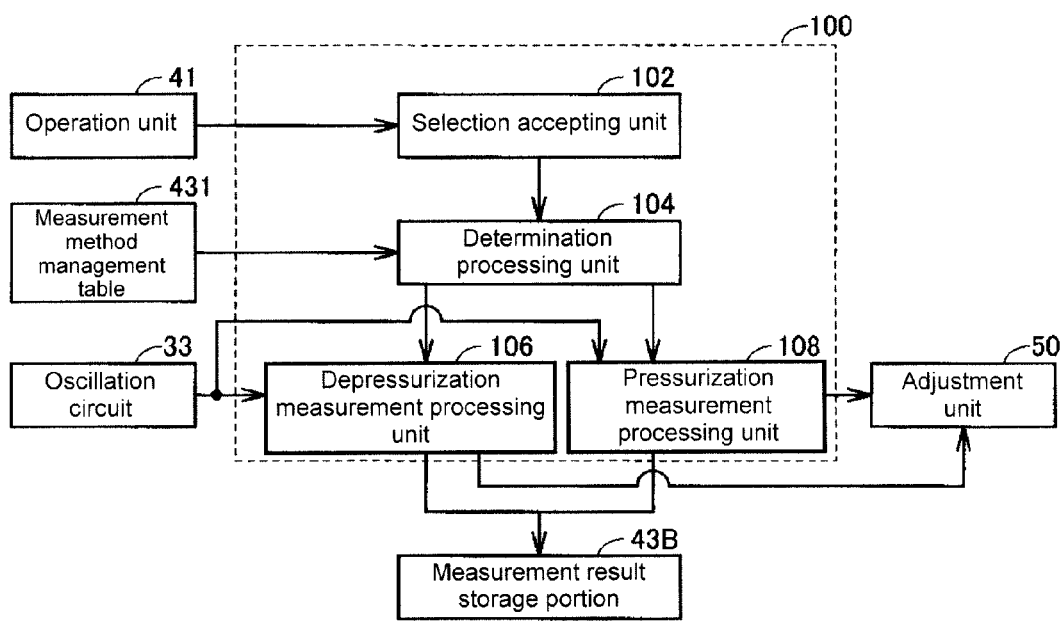
FIG. 5 is a function block diagram showing the function configuration of the electronic sphygmomanometer according to the first embodiment of the present invention.

FIG. 5 is a function block diagram showing the function configuration of the sphygmomanometer 1 according to the first embodiment of the present invention.

With reference to FIG. 5, the CPU 100 includes a selection accepting unit 102, a determination processing unit 104, a depressurization measurement processing unit 106, and a pressurization measurement processing unit 108. In FIG. 5, only the surrounding hardware that directly exchanges signals with each unit of the CPU 100 is shown to simplify the description.

The selection accepting unit 102 accepts the selection of the user through the operation unit 41. More specifically, the selection of the user identification information of the person to be measured for this time is accepted out of a plurality of user identification information set in advance based on the signal from the operation unit 41. The person to be measured for this time is thereby specified.

The determination processing unit 104 determines with which measurement method, the depressurization measurement method or the pressurization measurement method, to measure the blood pressure in accordance with the specified person to be measured. Specifically, the measurement method is determined for every person to be measured based on the content of the measurement method management table 431 and the input information from the operation unit 41. In the present embodiment, the input information is the information regarding the biological conditions of the person to be measured, and more specifically, the information on whether or not pregnant.

In the present embodiment, the measurement method desired by the user is determined for the measurement method for this time if the user sets the measurement method switching function to invalid. If the user sets the measurement method switching function to valid, the pressurization measurement method in which the measurement accuracy can be maintained high if the person to be measured is pregnant is determined for the measurement method for this time. Thus, the measurement method suited for the person to be measured (suited for the biological condition of the person to be measured) can be set for every measurement.

The depressurization measurement processing unit 106 is connected to the oscillation circuit 33 and the adjustment unit 50, and performs the measurement process of the blood pressure in the process of depressurization. The depressurization measurement processing unit 106 starts the process when determined by the determination processing unit 104 to measure the blood pressure with the depressurization measurement method. The process by the depressurization measurement processing unit 106 may be realized through a known method. In the present embodiment, after pressurizing at high speed to a predetermined value (e.g., 200 mmHg) and reaching the predetermined value, the pressurization is stopped to transition to the depressurization control. In the process of depressurization at slow speed, the systolic blood pressure and the diastolic blood pressure are measured (calculated) by applying a predetermined algorithm on the pulse wave amplitude superimposed on the cuff pressure based on the output signal from the oscillation circuit 33. The speed at the time of pressurization is faster than at least the speed at the time of depressurization.

The pressurization measurement processing unit 108 is connected to the oscillation circuit 33 and the adjustment unit 50, and performs the measurement process of the blood pressure in the process of pressurization. The pressurization measurement processing unit 108 starts the process when determined by the determination processing unit 104 to measure the blood pressure with the pressurization measurement method. The process by the pressurization measurement processing unit 108 may also be realized through a known method. According to the present embodiment, for example, in the process of pressurization at slow speed, the systolic blood pressure and the diastolic blood pressure are measured (calculated) by applying a predetermined algorithm on the pulse wave amplitude superimposed on the cuff pressure based on the output signal from the oscillation circuit 33. The pressurization is stopped and the air is exhausted rapidly after the systolic blood pressure and the diastolic blood pressure are calculated.

The blood pressure values measured by the depressurization measurement processing unit 106 and the pressurization measurement processing unit 108 are output to the measurement result storage portion 43B and the display unit 40.

The operation of each function block may be realized by executing the software stored in the memory 42, or at least one of which may be realized by hardware.

<Regarding Operation>

The operation of the sphygmomanometer 1 according to the present embodiment will now be described.

Figure 6:
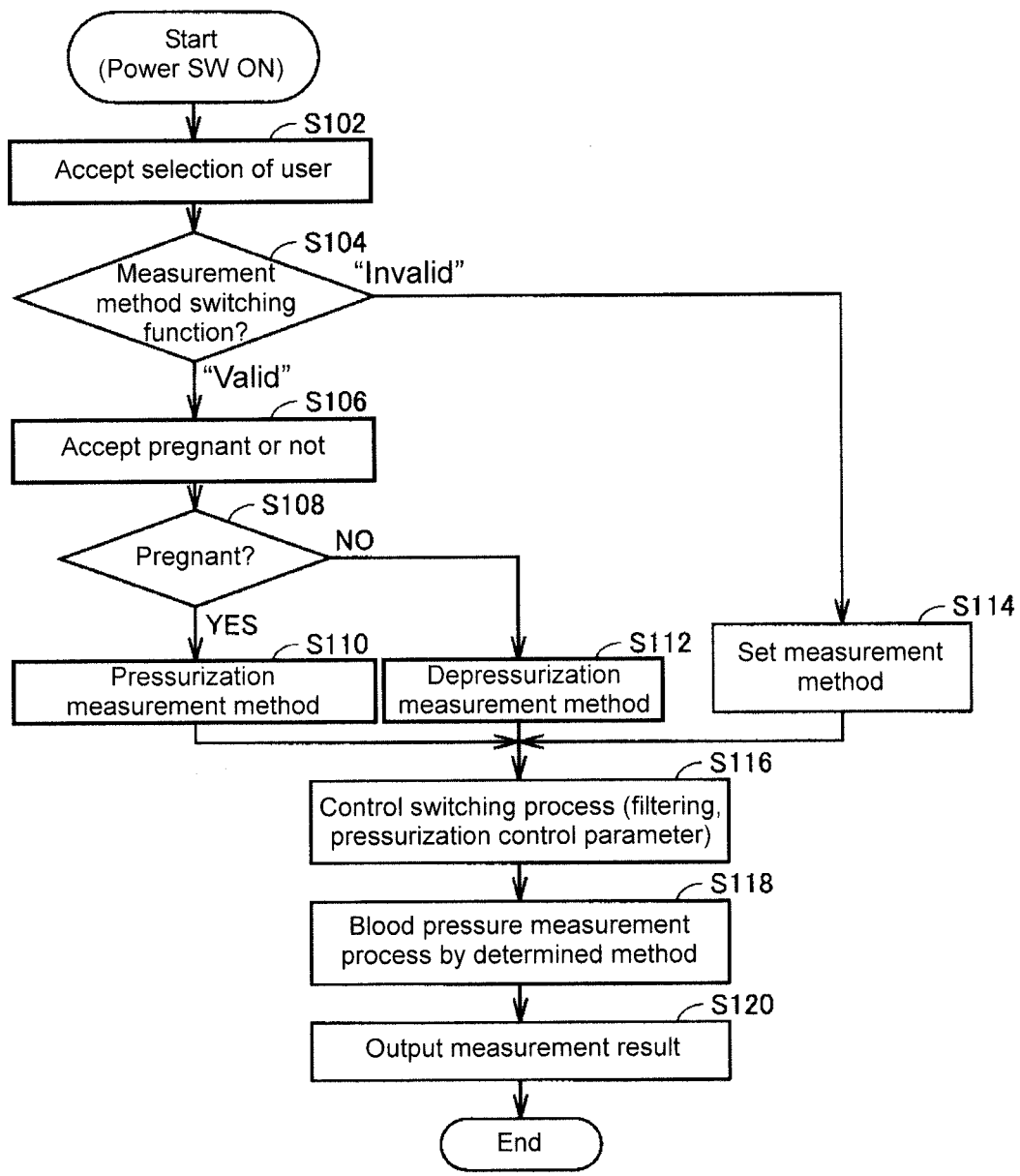
FIG. 6 is a flowchart showing the flow of the blood pressure measurement control in the first embodiment of the present invention.

FIG. 6 is a flowchart showing the flow of the blood pressure measurement control in the first embodiment of the present invention. The processes shown in the flowchart of FIG. 6 are stored in the memory 42 in advance as a program, and the CPU 100 reads out and executes such program to realize the function of the blood pressure measurement control.

With reference to FIG. 6, when the power switch 41A is pushed by the user, the selection accepting unit 102 accepts the user selection (step S102). Specifically, the selection accepting unit 102 displays a plurality of user identification information (e.g., user A, B, . . . ) on the display unit 40 to have the user select one of the user identification information.

The determination processing unit 104 then references the measurement method management table 431, and determines whether the person to be measured for this time, that is, the person to be measured specified by the selected user identification information has set the measurement method switching function to valid (step S104). That is, whether or not the information "valid" is stored in the measurement method switching function item 72 corresponding to the selected user identification information is determined.

If determined that valid is set ("valid" in step S104), the process proceeds to step S106. If determined that invalid is set ("invalid" in step S104), the process proceeds to step S114.

The determination processing unit 104 accepts the input of whether or not pregnant from the user in step S106.

Figure 7:
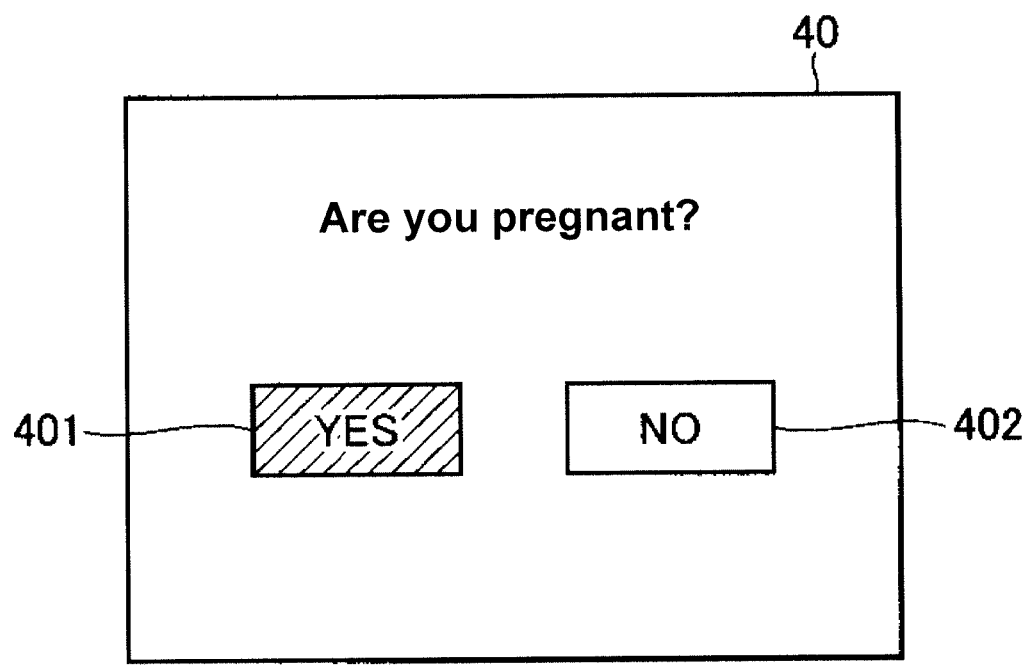
FIG. 7 is a view showing one example of a screen displayed in step S106 of FIG. 6.

FIG. 7 is a view showing one example of a screen displayed in step S106 of FIG. 6.

For instance, with reference to FIG. 7, a message "are you pregnant?" is displayed on the display unit 40, and a button 401 indicating "YES" and a button 402 indicating "NO" are also displayed.

If determined that the person to be measured is pregnant, that is, if determined that the YES button 401 is pushed (YES in step S108), the determination processing unit 104 determines that the measurement method corresponding to the person to be measured is the pressurization measurements method (step S110). This is because the blood pressure can be more accurately measured with the pressurization measurement method in the case of pregnant women, as described above.

If determined that the person to be measured is not pregnant, that is, if determined that the NO button 402 is pushed (NO in step S108), the measurement method is determined as the depressurization measurement method (step S112). The determination is made as the depressurization measurement method because the default (initial setting) measurement method of the sphygmomanometer 1 according to the present embodiment is the depressurization measurement method.

Since there is basically no difference in the measurement result between the measurement methods if not the case of pregnant women, the measurement method may not necessarily be the depressurization measurement method. Therefore, the user may select which measurement method the user desires if the user is not a pregnant woman.

Alternatively, assume the information of one of the measurement methods is stored in the desired measurement method item 73 even though the measurement method switching function is valid in the measurement method management table 431. In such a case, the method complying with the desired measurement method may be determined as the measurement method for this time.

In step S114, the determination processing unit 104 determines the measurement method set in advance, that is, the measurement method stored in the desired measurement method item 73 of the measurement method management table 431 as the measurement method suited for the person to be measured.

After the process of steps S110, S112, or S114 is finished, the control switching process is executed (step S116), and the blood pressure measurement process by the determined method is executed (step S118).

In step S116, insert/delete of the filtering process in the pressurization process, and change of control parameter are carried out. The filtering process on the signal from the oscillation circuit 33 (noise removal of noise of the pump 51) is not necessary in the pressurization process in the case of the depressurization measurement method, but is necessary in the case of the pressurization measurement method. Furthermore, the pressurization is carried out at slow speed in the case of the pressurization measurement method, but the control parameter is changed in the case of the depressurization measurement method since the pressurization needs to be carried out at higher speed than in the pressurization measurement method.

In step S118, the process by the depressurization measurement processing unit 106 is executed if the determined method is the depressurization measurement method. The process by the pressurization measurement processing unit 108 is executed if the determined method is the pressurization measurement method.

The control switching process is executed in step S116 on the assumption that the control parameter and the like in the previous measurement (regardless of the person to be measured) is stored in a predetermined region of the flash memory 43, and such process is not essential. That is, the program corresponding to the determined measurement method may be read out from the memory 42 for each measurement, and each process may be executed.

After the blood pressure is measured with one of the measurement methods, the measurement result is output to the flash memory 43 and the display unit 40 (step S120).

The blood pressure measurement control according to the present embodiment is thereby terminated.

Therefore, according to the present embodiment, the blood pressure is measured with the pressurization measurement method if the person to be measured is a pregnant woman if the measurement method switching function is set to valid. Therefore, the blood pressure can be accurately measured regardless of whether the person to be measured is pregnant or not.

The person to be measured may feel uncomfortable with the pressurization measurement method even if that person is pregnant. In the present embodiment, the user can set valid/invalid of the measurement method switching function in advance, and the desired measurement method can be adopted if set to invalid regardless of whether the person to be measured is pregnant. Therefore, the measurement method can be flexibly determined for every person to be measured.

In the present embodiment, the valid/invalid of the measurement method switching function is set in advance, but this is not the sole case. For instance, whether pregnant or not may be determined first, and then the desired measurement method stored in the measurement method management table 431 may be determined as the measurement method for this time when determined as not pregnant.

Alternatively, the measurement method management table 431 itself is not essential, and which method is desired may be selected every time when determined as not pregnant.

In the present embodiment, whether pregnant or not is selected by the user every time, but such information may be further stored in the measurement method management table 431. In such a case, when the measurement starts, the information on whether or not pregnant corresponding to the user is read out in step S106, and whether or not the user is pregnant may be determined (S108) based on such information.

[Second Embodiment]

A second embodiment of the present invention will now be described.

In the first embodiment, the measurement method is determined from the standpoint of measurement accuracy. In the present embodiment, on the other hand, the measurement method is determined from the standpoint of measurement time. The "measurement time" is the time from the start of pressurization of the cuff to the end of depressurization of the cuff.

The configuration and the basic operation of the sphygmomanometer according to the present embodiment are similar to the first embodiment. Therefore, the description will be made using the reference numerals used in the first embodiment.

Only the portion different from the first embodiment will be described below.

Figure 8:
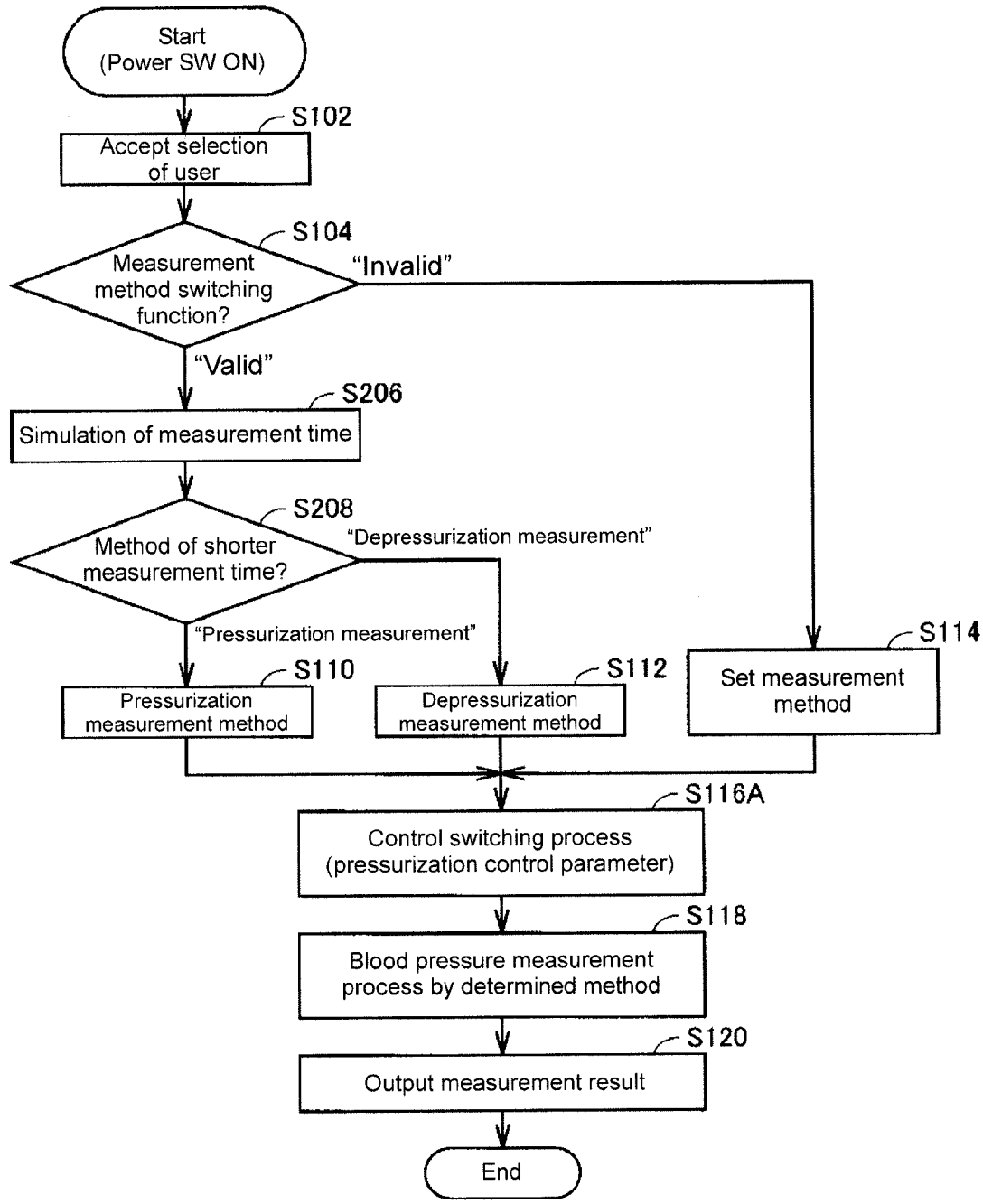
FIG. 8 is a flowchart showing the conceptual flow of the blood pressure measurement control according to a second embodiment of the present invention.

FIG. 8 is a flowchart showing the conceptual flow of the blood pressure measurement control according to the second embodiment of the present invention. The same step numbers are denoted for the processes similar to the flowchart of FIG. 6. Therefore, the description thereon will not be repeated.

The processes of steps S206 and S208 are executed in place of the processes of steps S106 and S108 of FIG. 6 with reference to FIG. 8. The process of step S116A is executed in place of the process of step S116.

If determined that "valid" is set in step S104, the determination processing unit 104 executes a simulation of the measurement time based on the past measurement value of the user stored in the measurement result storage portion 43B (step S206). The process proceeds to step S110 if the method with shorter measurement time is the pressurization measurement method, and the process proceeds to step S112 if the method with shorter measurement time is the depressurization measurement method.

In the present embodiment, the depressurization measurement processing unit 106 estimates the systolic blood pressure in the pressurization process, and transitions to the depressurization control at slow speed when the systolic blood pressure is estimated. The pressurization measurement processing unit 108 depressurizes, that is, exhausts, rapidly when the systolic blood pressure is detected in the pressurization process at slow speed. This will be more specifically described with reference to FIGS. 9A and 9B.

FIGS. 9A and 9B are views showing the difference in the maximum pressure value by the pressurization measurement method and the depressurization measurement method. FIG. 9A shows the control pressure value in the pressurization measurement method along the time axis. FIG. 9B shows the control pressure value in the depressurization measurement method along the time axis.

With reference to FIG. 9A, since the blood pressure is measured in the pressurization process in the pressurization measurement method, the pressurization control is performed at slow speed and with the pressure change amount per predetermined time set constant. The blood pressure value, that is, the diastolic blood pressure and the systolic blood pressure are measured (calculated) in real time in parallel to the pressurization control. The pressurization control is stopped after the systolic blood pressure is calculated, and then transitions to the rapid depressurization. Representing the systolic blood pressure calculated in the pressurization process as the pressure value SYS, the maximum pressure value MAXa takes a value barely different from the pressure value SYS.

With reference to FIG. 9B, since the blood pressure is measured in the depressurization process in the depressurization measurement method, the control is performed such that the speed in the pressurization process is faster than the speed in the depressurization process (pressure change amount per predetermined time). The systolic blood pressure is estimated in parallel to the pressurization control. After the systolic blood pressure is estimated, the pressurization control is stopped at the time point of estimated systolic blood pressure+predetermined value (e.g., 40 mmHg), and then transitions to the depressurization at slow speed. Representing the systolic blood pressure estimated in the pressurization process as the pressure value E_SYS, the pressure stops at a pressure value MAXb higher than the pressure value E_SYS by a predetermined value.

Therefore, in step S116A, the switching of the filter in the pressurization process may not be carried out since the detection process of the blood pressure is executed in the pressurization process in both measurement methods.

Specific examples of the blood pressure measurement control according to the present embodiment will be described below.

(First Specific Example)

FIGS. 10A and 10B are views showing the difference in measurement time by the pressurization measurement method and the depressurization measurement method for when the systolic blood pressure is high. FIG. 10A shows the control pressure value of when measured in the pressurization measurement method along the time axis. FIG. 10B shows the control pressure value of when measured in the depressurization measurement method along the time axis.

When the pressurization measurement method is applied to the person to be measured whose systolic blood pressure is high, the pressurization is carried out at equal speed (and slow speed) until the systolic blood pressure is detected, and thus the measurement time becomes longer than with the depressurization measurement method in which the pressurization is carried out at once up to around the systolic blood pressure. Therefore, although the pressurization measurement method is the default measurement method, the measurement time can be shortened by switching to the depressurization measurement method with respect to the person to be measured whose systolic blood pressure is higher than or equal to a predetermined value.

In the first specific example of the present embodiment, the measurement method is determined by such view point.

Figure 11:
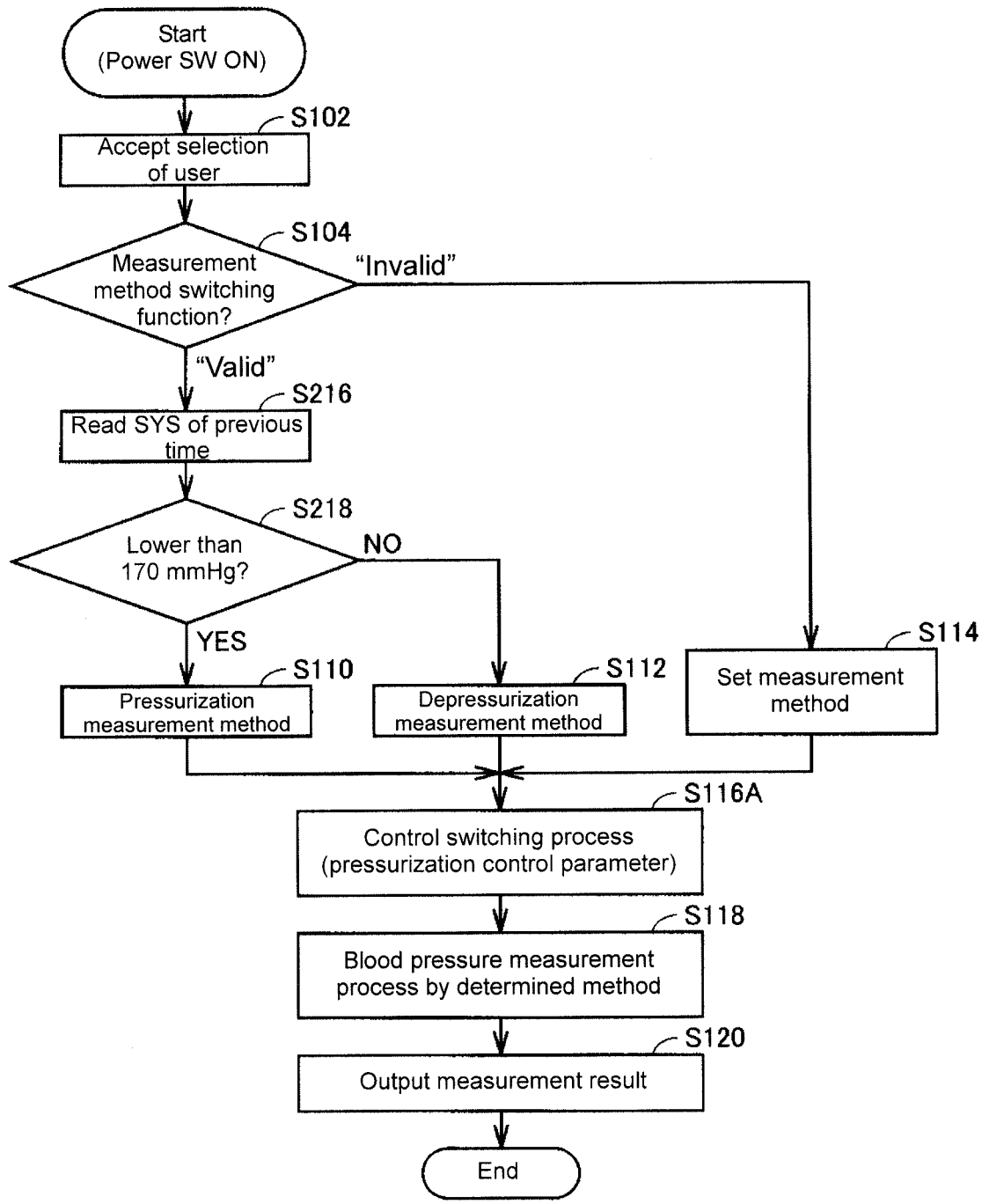
FIG. 11 is a flowchart showing the flow of the first specific example of the blood pressure measurement control in the second embodiment of the present invention.

FIG. 11 is a flowchart showing the flow of the first specific example of the blood pressure measurement control in the second embodiment of the present invention. In FIG. 11, steps S216 and S218 are executed in place of steps S206 and S208 of FIG. 8.

With reference to FIG. 11, the systolic blood pressure of the previous time, for example, is read from the measurement result storage portion 43B in step S216. More specifically, the systolic blood pressure data contained in the measurement result data of the most recent date and time of the measurement result data stored in correspondence with the user identification information selected in step S102 is read out.

In step S218, whether or not the read systolic blood pressure is lower than a predetermined value such as 170 mmHg is determined. The process proceeds to step S110 if the systolic blood pressure is lower than 170 mmHg, and the process proceeds to step S112 if the systolic blood pressure is higher than or equal to 170 mmHg. That is, if the systolic blood pressure is higher than or equal to 170 mmHg, determination is made that the measurement time is shorter with the depressurization measurement method, and the measurement method for this time is set to the depressurization measurement method.

Assume that the pressurization measurement method is adopted if the systolic blood pressure is lower than 170 mmHg because the default measurement method of the sphygmomanometer 1 is the pressurization measurement method in the first specific example of the present embodiment. Similar to when not pregnant in the first embodiment, there is basically no difference in the measurement result regardless of which measurement method is adopted, and the measurement time does not become excessively long, and hence the measurement method may not necessarily be the pressurization measurement method.

(Second Specific Example)

Figure 12:
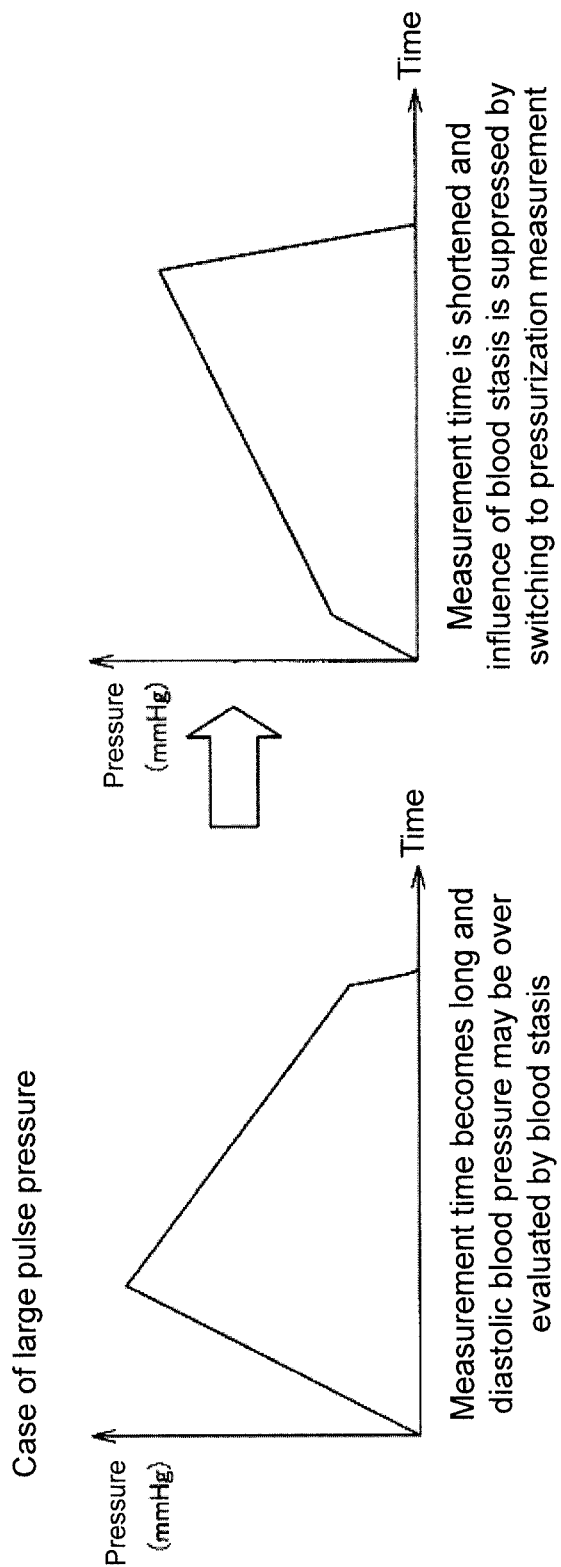
FIGS. 12A and 12B are views showing the difference in the measurement time by the depressurization measurement method and the pressurization measurement method when the pulse pressure is high.

FIGS. 12A and 12B are views showing the difference in the measurement time by the depressurization measurement method and the pressurization measurement method when the pulse pressure (difference value of the systolic blood pressure and diastolic blood pressure) is large. FIG. 12A shows the control pressure value when measured in the depressurization measurement method along the time axis. FIG. 12B shows the control pressure value when measured in the pressurization measurement method along the time axis.

When the depressurization measurement method is applied to the person to be measured whose pulse pressure is large, the measurement time becomes longer than the person whose pulse pressure is not high for the restraining time in the depressurization process since the depressurization is continued at equal speed until the diastolic blood pressure is detected in the depressurization process. Accompanied therewith, the influence due to blood stasis may be reflected on the measurement value. Specifically, the diastolic blood pressure may be over evaluated.

Therefore, although the depressurization measurement method is the default measurement method, the measurement time can be reduced by switching to the pressurization measurement method with respect to the person to be measured whose pulse pressure is greater than or equal to a predetermined value. The measurement accuracy can also be enhanced.

In the second specific example of the present embodiment, the measurement method is determined by such view point.

Figure 13:
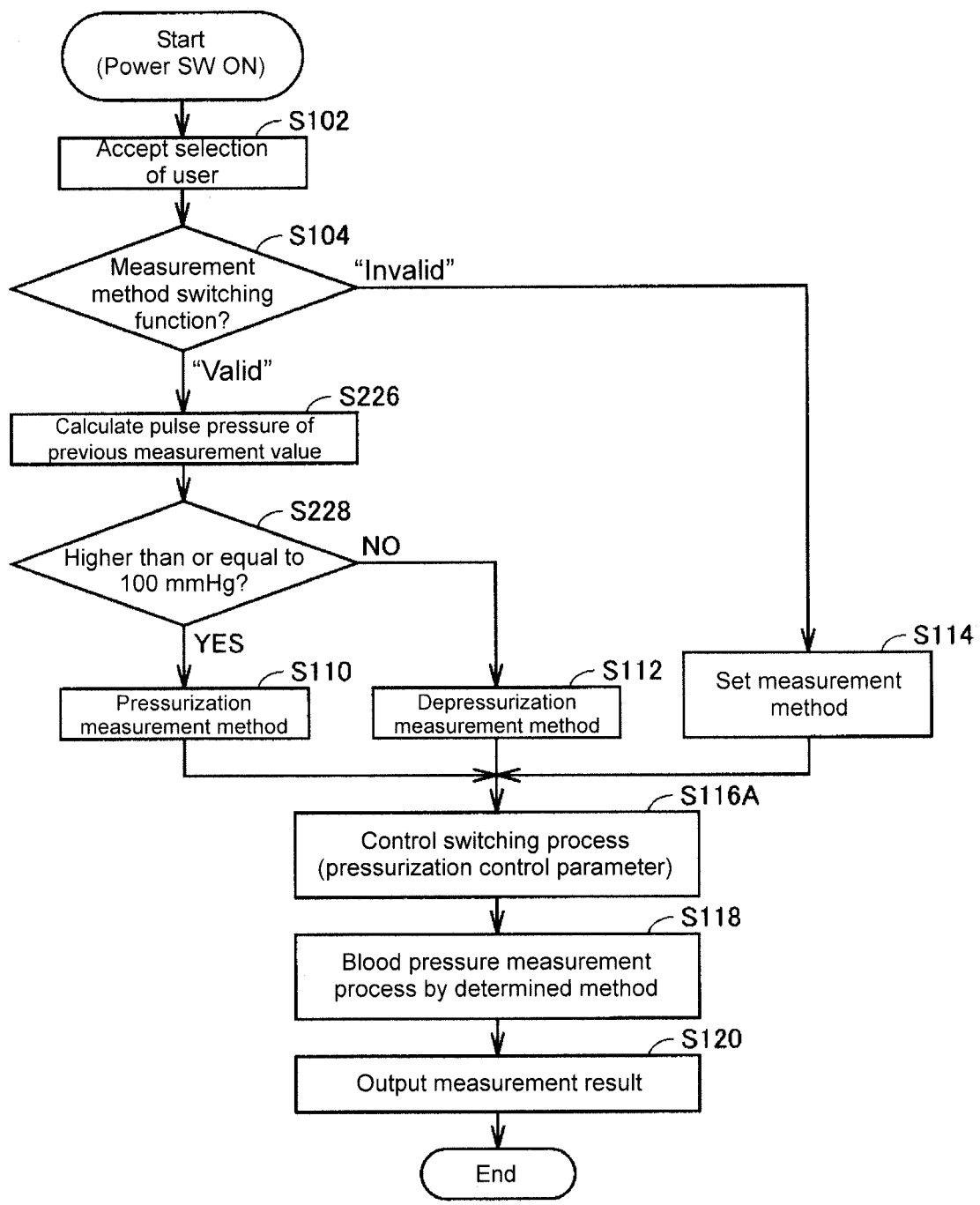
FIG. 13 is a flowchart showing the flow of the second specific example of the blood pressure measurement control in the second embodiment of the present invention.

FIG. 13 is a flowchart showing the flow of the second specific example of the blood pressure measurement control in the second embodiment of the present invention. In FIG. 13, steps S226 and S228 are executed in place of steps S206 and S208 of FIG. 8.

With reference to FIG. 11, the pulse pressure of the previous time is calculated based on the measurement result data of the previous time and the like of the measurement result storage portion 43B in step S226. More specifically, the systolic blood pressure data and the diastolic blood pressure data contained in the measurement result data of the most recent date and time of the measurement result data stored in correspondence with the user identification information selected in step S102 are read out. The difference between the read systolic blood pressure and the diastolic blood pressure is the pulse pressure of the previous time.

In step S228, whether or not the calculated pressure value is greater than or equal to 100 mmHg is determined. The process proceeds to step S110 if the pulse pressure is higher than or equal to 100 mmHg, and the process proceeds to step S112 if the pulse pressure is lower than 100 mmHg. That is, if the pulse pressure is higher than or equal to 100 mmHg, determination is made that the measurement time is shorter with the pressurization measurement method, and the measurement method for this time is set to the pressurization measurement method.

Assume that the depressurization measurement method is adopted if the pulse pressure is lower than 100 mmHg because the default measurement method of the sphygmomanometer 1 is the depressurization measurement method in the second specific example of the present embodiment. Similar to when not pregnant in the first embodiment, there is basically no difference in the measurement result regardless of which measurement method is adopted, and the measurement time does not become excessively long, and hence the measurement method may not necessarily be the depressurization measurement method.

(Variant)

In the embodiment described above, the measurement method with which the measurement time becomes shorter is determined based on the past measurement result of the person to be measured. However, not limited to the past measurement result, the measurement method with which the measurement time becomes shorter may be determined based on the information regarding the biological conditions of the person to be measured.

Figure 14:
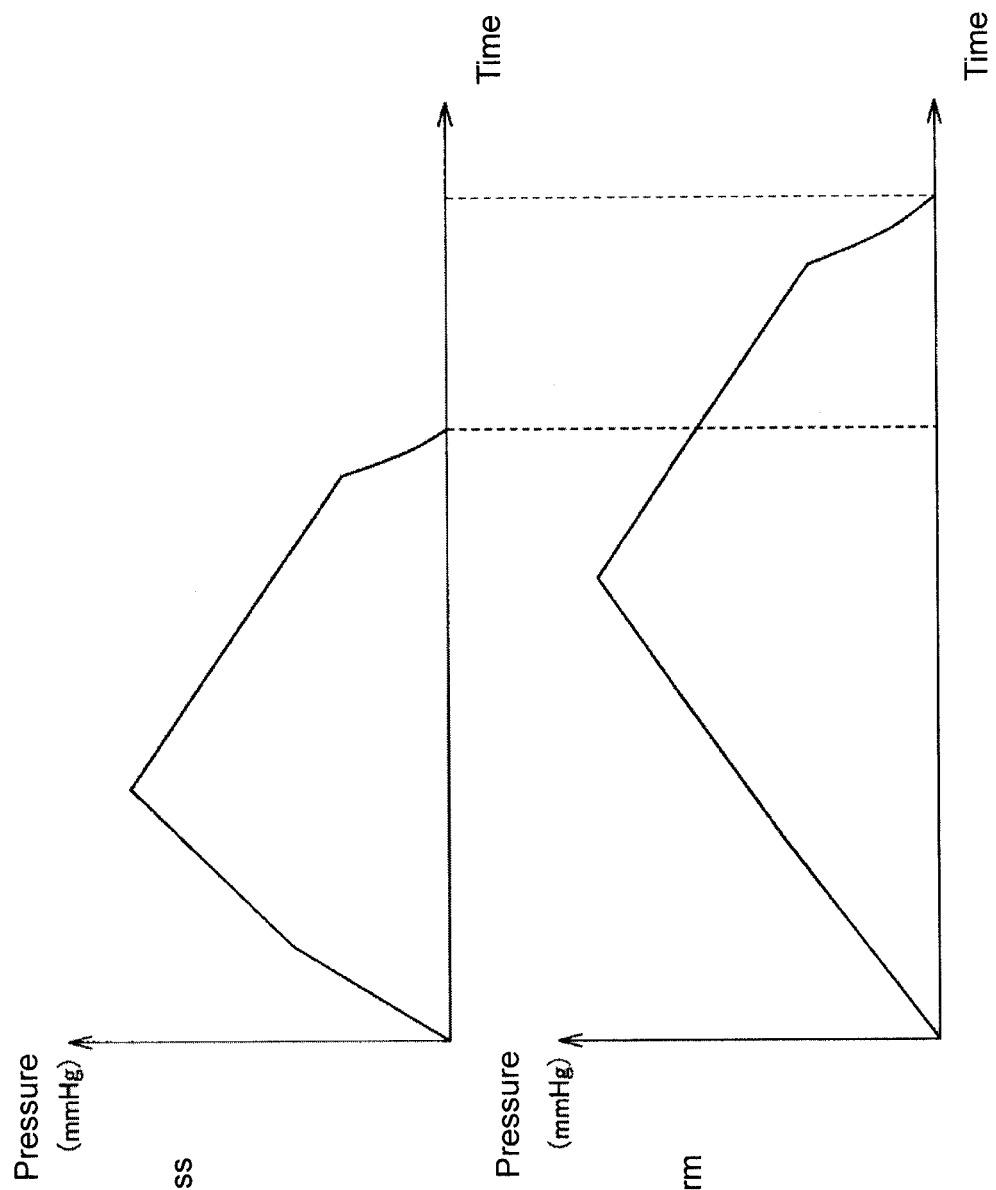
FIGS. 14A and 14B are views describing the influence of the measurement time due to the difference in the arm periphery (peripheral length of measurement site) for the case of the depressurization measurement method.

FIGS. 14A and 14B are views describing the influence of the measurement time due to the difference in the arm periphery for the case of the depressurization measurement method. In FIG. 14A, the control pressure value for the case of the arm of standard thickness is shown along the time axis. In FIG. 14B, the control pressure value for the case of thick arm is shown along the time axis.

Since the flow rate of the pump 51 is limited, the initial pressurization time becomes longer if the arm is thick (i.e., if the peripheral length of the measurement site is long). As a result, the entire measurement time becomes long. This can be avoided if the flow rate of the pump 51 is large, but this will enlarge the component thereby leading to increase in cost. Thus, if the flow rate of the pump 51 is limited, the measurement time can be shortened with the pressurization measurement method of pressurizing at slow speed with respect to the person to be measured with thick arm.

Therefore, although the depressurization measurement method is the default measurement method, the measurement time can be shortened by switching to the pressurization measurement method with respect to the person to be measured with thick arm.

In the variant of the present embodiment, the measurement method is determined by such view point. Whether the arm is thick or not can be determined by whether the arm periphery is greater than or equal to a predetermined value (e.g., 32 cm). Alternatively, when attaching a cuff (not shown) for thick arm in place of the cuff 20 shown in FIG. 1, the arm of the person to be measured may be determined as thick if the attachment of the cuff for thick arm is detected. In the latter case, a separate unit (not shown) including the cuff for thick arm and the air tube for thick arm is assumed to exist. In such a case, whether or not the cuff for thick arm is attached can be detected by changing the length of the plug of the air tube for thick arm and the length of the plug of the standard air tube 31.

Figure 15:
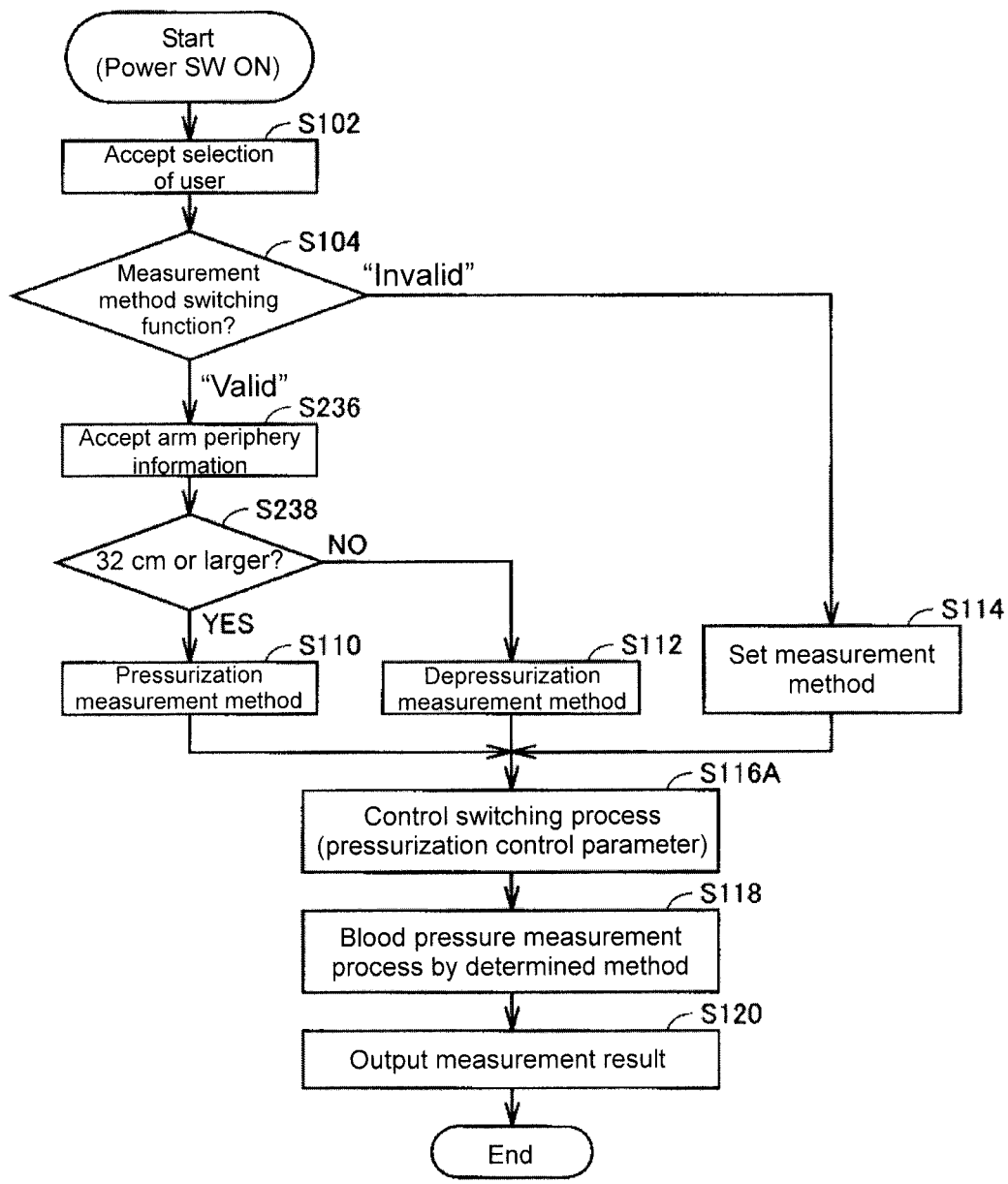
FIG. 15 is a flowchart showing the blood pressure measurement control according to a variant of the second embodiment of the present invention.

FIG. 15 is a flowchart showing the blood pressure measurement control according to a variant of the second embodiment of the present invention. In FIG. 15, steps S236 and S238 are executed in place of steps S206 and S208 of FIG. 8.

With reference to FIG. 15, the determination processing unit 104 accepts the input of the arm periphery information as the information indicating the biological condition of the person to be measured from the user in step S236.

Figure 16:
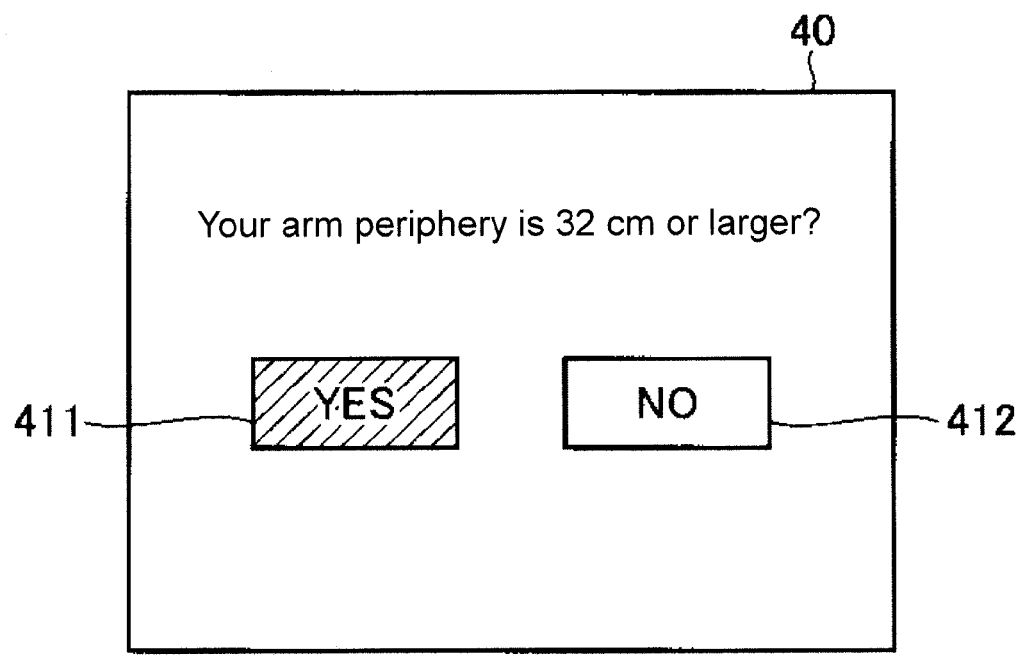
FIG. 16 is a view showing one example of a screen displayed in step S236 of FIG. 15.

FIG. 16 is a view showing one example of a screen displayed in step S236 of FIG. 15.

With reference to FIG. 16, a message such as "your arm periphery is 32 cm or larger" is displayed on the display unit 40, and a button 411 indicating "YES" and a button 412 indicating "NO" are also displayed.

If determined that the arm periphery is 32 cm or larger, that is, if determined that the YES button 411 is pushed (YES in step S238), the process proceeds to step S110. If determined that the arm periphery is smaller than 32 cm, that is, if determined that the NO button 412 is pushed (NO in step S238), the process proceeds to step S112. That is, when the information that the arm periphery is 32 cm or larger is input, determination is made that the measurement time is shorter in the pressurization measurement method, and the measurement method for this time is set to the pressurization measurement method.

The depressurization measurement method is adopted if determined that the arm periphery is smaller than 32 cm because the default measurement method of the sphygmomanometer 1 according to the variant of the present embodiment is the depressurization measurement method. Since there is basically no difference in the measurement result between the measurement results in this case, similar to when not pregnant in the first embodiment, and the measurement time does not become excessively long, the measurement method may not necessarily be the depressurization measurement method.

Since the site to wrap around the cuff 20, that is, the measurement site is the arm in the present embodiment, determination is made with the thickness of the arm but whether or not the peripheral length of the measurement site is greater than or equal to a predetermined value may be determined. That is, determination is made with the peripheral length (thickness) of the wrist if the measurement site is the wrist.

As described above, according to the present embodiment, the measurement method can be determined so that the measurement time does not become long based on the past measurement value of the person to be measured or the biological condition (whether thick arm or not) of the person to be measured. Therefore, the restraining time of the person to be measured can be shortened, and as a result, the lowering of the motivation to the blood pressure measurement of the person to be measured can be prevented.

Similar to the first embodiment, the measurement method is determined while prioritizing the wish of the person to be measured. Therefore, the appropriate measurement method can be flexibly determined for every person to be measured.

The processes of the first and second specific examples and the variant shown in the present embodiment may be combined. Furthermore, the processes of each example of the present embodiment and the processes of the first embodiment may be combined. Determination may be made as the pressurization measurement method if one of the conditions of during pregnancy and thick arm is satisfied. The height of the systolic blood pressure, the magnitude of the pulse pressure, and the like may be determined if not during pregnancy, and the measurement method may be determined according to the determination result.

The depressurization measurement method is set with respect to the person to be measured whose systolic blood pressure is high since the measurement method is determined from the standpoint of shortening the measurement time in the present embodiment, but the pressurization measurement method is desirable from the standpoint of alleviating the pain by compression. This will be described with reference again to FIGS. 9A and 9B.

With reference to FIGS. 9A and 9B, the difference between the pressure value SYS and the maximum pressure value MAXa in the pressurization measurement method is expressed as "ΔPa", and the difference between the pressure value E_SYS and the maximum pressure value MAXb in the depressurization measurement method is expressed as "ΔPb". Here, ΔPa is an extent of an error, and ΔPa is a predetermined value (between 10 and 40 mmHg). Thus, the maximum pressure value MAXb takes a value greater than the maximum pressure value MAXa. Therefore, if the depressurization measurement method is adopted with respect to the person to be measured whose systolic blood pressure is high, an excessive compression becomes necessary which may give pain.

The pressurization measurement method is more desirable from the standpoint of alleviating the pain by compression.

Whether to shorten the measurement time, whether to enhance the measurement accuracy, and whether to alleviate the pain by compression differ depending on the person to be measured or for every measurement even if on the same person to be measured. Therefore, the desired criterion may be stored in the measurement method management table 431, and the measurement method may be determined by the criterion desired by the user in the measurement. Alternatively, the user may select whether or not to perform the automatic switching (determination) of the measurement method from which standpoint (criterion) for every measurement.

In the first and second embodiments, the measurement method used in the measurement may be displayed on the display unit 40. Specifically, in step S120 of each flowchart, the information for specifying the measurement method (i.e., determination result of the measurement method) used in the measurement of the pressurization measurement method and the depressurization measurement method may be displayed on the display unit 40 by the CPU 100. For instance, if measured with the presence of a doctor in a hospital, the doctor can check with which measurement method the blood pressure value being displayed is measured.

Similarly, the information for identifying the determination result of the measurement method is stored in the flash memory 43 in association with the measurement value in step S120 of each flowchart. Even when the person to be measured is measured outside the hospital, with which measurement method the blood pressure value is measured can be grasped when the doctor checks the measurement result later. In this case, specifically, the determination result data Mi shown in FIG. 3 may further include the data MMi representing the measurement method.

The doctor can estimate the reliability and the like of the measurement value by displaying and/or recording the method used in the measurement. For instance, the reliability of the measurement value is presumed to be not very high if measured with the depressurization measurement method although the person to be measured is pregnant.

[Third Embodiment]

In the first and second embodiments, the measurement method is automatically determined based on the biological condition (pregnant, thick arm) of the person to be measured or the past measurement value, but the results actually measured with both measurement methods may be compared and the appropriately measurement method (hereinafter referred to as "recommended measurement method") may be determined for every person. This mode will be described as a third embodiment.

The configuration of the sphygmomanometer according to the present embodiment is similar to the first embodiment. Therefore, the description will also be made here using the reference numerals used in the first embodiment.

Only the portion different from the first embodiment will be described.

Figure 17:
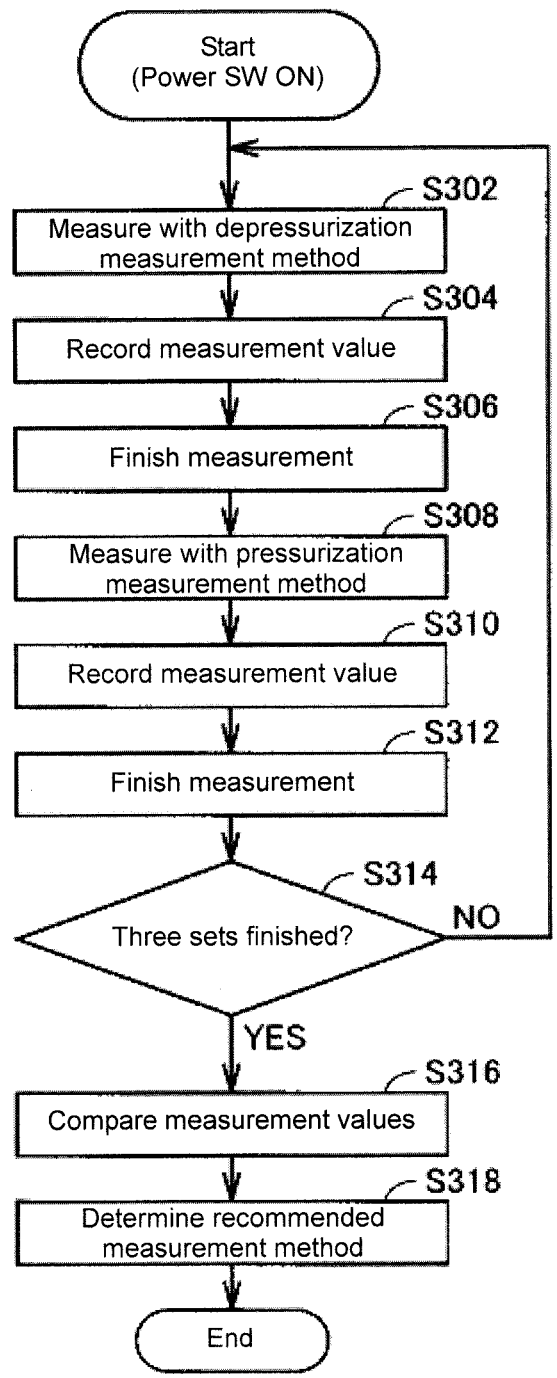
FIG. 17 is a flowchart showing a determination process of the recommended measurement method according to a third embodiment of the present invention.

FIG. 17 is a flowchart showing a determination process of the recommended measurement method according to a third embodiment of the present invention. The processes shown in the flowchart of FIG. 17 are stored in the memory 42 in advance as a program, and the CPU 100 reads out and executes such program to realize the function of determination of the recommended measurement method. The determination process is not performed for every measurement, and is executed only when the user turns ON the power switch 41A and the user instructs the execution of the function of the determination process.

With reference to FIG. 17, the depressurization measurement processing unit 106 measures the blood pressure with the depressurization measurement method (step S302). The measured blood pressure value is recorded in the internal memory as a measurement value with the depressurization measurement method (step S304). After the measurement with the depressurization measurement method is finished (step S306), the pressurization measurement processing unit 108 measures the blood pressure with the pressurization measurement method (step S308). The measured blood pressure value is recorded in the internal memory as a measurement value with the pressurization measurement method (step S310). After the measurement with the pressurization measurement method is finished (step S312), the process proceeds to step S314.

In step S314, whether or not the measurement with the depressurization measurement method and the measurement with the pressurization measurement method are finished for three sets is determined. If three sets are not finished (NO in step S314), the process returns to step S302 and the above process is repeated. If determined as repeated for three sets (YES in step S314), the process proceeds to step S316.

In step S316, the CPU 100 compares the measurement values recorded in step S304 and S310. Specifically, the variation of the values measured three times is compared and the method with which the measurement value is more stable is determined as the recommended measurement method (step S318). Alternatively, the blood pressure value is compared with the blood pressure value measured through an auscultatory method by a medical staff, or representatively a doctor, and the measurement method closer to such blood pressure value is determined as the recommended measurement method. In the latter case, the blood pressure measured by the auscultatory method is assumed to be recorded in a predetermined region (not shown) of the flash memory 43. The medical staff may compare the blood pressure value determined through the auscultatory method and the blood pressure values measured with the measurement methods, and determine the recommended measurement method by hand.

The recommended measurement method determined in such manner may be newly added to the measurement method management table 431. In this case, the determination processing unit 104 determines the recommended measurement method recorded in the measurement method management table 431 as the measurement method suited for the user when the measurement method switching function is set to valid ("valid" in step S104 of FIG. 6).

As described above, there is no great difference in the result regardless of which measurement method is used for the measurement if the person to be measured is not pregnant, but although rare, there are some cases where there is a difference in the result. According to the present embodiment, the measurement method of higher measurement accuracy is reliably set as the recommended measurement method since the recommended measurement method is defined by comparing the actual measurement results. As a result, the blood pressure can be measured with the measurement method suited for the person to be measured.

The blood pressure measurement method performed by the sphygmomanometer according to one or more embodiments of the present invention may be provided as a program. Such program may be recorded in an optical medium such as a CD-ROM (Compact Disc-ROM) or a computer readable recording medium such as a memory card, and provided as a program product. The program may be provided by being downloaded through a network.

The embodiments disclosed herein are illustrative in all aspects and should not be construed as being restrictive. While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF SYMBOLS 1 electronic sphygmomanometer
10 main body
20 cuff
21 air bag
30 air system
31 air tube
32 pressure sensor
33 oscillation circuit
40 display unit
41 operation unit
41A power switch
41B measurement switch
41C set switch
41D cursor switch
42 memory
43 flash memory
43A user information storage portion
43B measurement result storage portion
44 power supply
45 timing unit
46 data input/output unit
50 adjustment unit
51 pump
52 valve
53 pump drive circuit
54 valve drive circuit
100 CPU
102 election accepting unit
104 determination processing unit
106 depressurization measurement processing unit
108 pressurization measurement processing unit
132 recording medium
431 measurement method management table

The invention claimed is:
1. An electronic sphygmomanometer for measuring a blood pressure according to an oscillometric method, the electronic sphygmomanometer comprising:
a cuff to be wrapped around a predetermined measurement site;
an adjustment unit for adjusting a pressure in the cuff by pressurization and depressurization;
a pressure detection unit for detecting a cuff pressure representing the pressure in the cuff; and
a control unit for performing a control for measuring the blood pressure;
wherein the control unit includes:
a determination unit for selecting a depressurization measurement method or a pressurization measurement method to measure the blood pressure according to a person to be measured,
a first measurement processing unit for measuring blood pressure using a depressurization process when the determination unit selects the depressurization measurement method, and
a second measurement processing unit for measuring blood pressure using a pressurization process when the determination unit selects the pressurization measurement method,
wherein during the pressurization process, the blood pressure is determined prior to any cuff depressurization,
wherein the electronic sphygmomanometer further comprises an input accepting unit for accepting input information from a user,
wherein the input information indicates whether an arm of the person to be measured is thick,
wherein the determination unit selects the depressurization or pressurization measurement method based on the input information, wherein the input accepting unit accepts information on whether or not an arm of the person to be measured is thick as the input information, and wherein the determination unit selects the pressurization measurement method if the input information indicates that the arm of the person to be measured is thick.

2. The electronic sphygmomanometer according to claim 1, further comprising:

a display unit for displaying the measurement result of the blood pressure, wherein the display unit further displays information for specifying the method selected for the measurement of the depressurization measurement method and the pressurization measurement method.

3. The electronic sphygmomanometer according to claim 1, wherein the first measurement processing unit transitions the performing of the measurement process to a depressurization control at slow speed when the systolic blood pressure is estimated in the pressurization process at a speed faster than the depressurization process from previous measurements.

4. The electronic sphygmomanometer according to claim 1, wherein the second measurement processing unit rapidly depressurizes when the systolic blood pressure is detected in the pressurization process at slow speed.

5. A method for measuring a blood pressure according to an oscillometric method using an electronic sphygmomanometer, comprising:

a wrapping step of wrapping a cuff of the electronic sphygmomanometer around a predetermined measurement site;

an adjustment step of adjusting via the electronic sphygmomanometer a pressure in the cuff by pressurization and depressurization;

a detecting step of detecting via the electronic sphygmomanometer a cuff pressure representing the pressure in the cuff; and a control step of performing a control for measuring the blood pressure via the electronic sphygmomanometer;

wherein the control step comprises:

a determination step of selecting a depressurization measurement method or a pressurization measurement method to measure the blood pressure according to a person to be measured, a first measurement step of performing a measurement process of the blood pressure in a depressurization process when selected by the determination step to measure the blood pressure with the depressurization measurement method, and a second measurement step of performing a measurement process of the blood pressure in a pressurization process when selected by the determination step to measure the blood pressure with the pressurization measurement method, wherein during the pressurization process, the blood pressure is determined prior to any cuff depressurization, wherein the method further comprises an input accepting step for accepting input information from a user via the electronic sphygmomanometer, wherein the determination step includes selecting the measurement method based on the input information, and wherein the determination step includes selecting the pressurization measurement method if the arm of the person to be measured is thick.

* * * * *